United States Patent [19]

Heiler

[11] Patent Number: 5,019,380

[45] Date of Patent: May 28, 1991

[54] NOVEL ANTIMICROBIAL COMPOSITIONS AND PROCESS FOR PREPARING THE SAME

[75] Inventor: David J. Heiler, Avon, N.Y.

[73] Assignee: Bausch & Lomb Incorporated, Rochester, N.Y.

[21] Appl. No.: 515,394

[22] Filed: Apr. 27, 1990

[51] Int. Cl.$^5$ .............................................. A61K 31/78
[52] U.S. Cl. ..................................... 424/81; 514/914; 514/912; 424/661
[58] Field of Search ........................... 424/81, 80, 661; 525/326.9

[56] References Cited

U.S. PATENT DOCUMENTS

| | | | |
|---|---|---|---|
| 4,113,857 | 9/1978 | Shetty | 424/150 |
| 4,125,602 | 11/1978 | Atasoy et al. | 424/80 |
| 4,235,884 | 11/1980 | Salkin | 424/150 |
| 4,684,519 | 8/1987 | Barabas | 424/80 |
| 4,731,192 | 3/1988 | Kenjo | 252/95 |

*Primary Examiner*—Thurman Page
*Assistant Examiner*—D. Gabrielle Phelan
*Attorney, Agent, or Firm*—Salvatore P. Pace

[57] ABSTRACT

Novel compositions of matter are provided herein which are the reaction product of polyvinylpyrrolidone and hypochlorites. These compositions are useful as antimicrobial agents.

16 Claims, No Drawings

NOVEL ANTIMICROBIAL COMPOSITIONS AND PROCESS FOR PREPARING THE SAME

BACKGROUND OF THE INVENTION

1. Field of the Invention

The present invention relates generally to novel antimicrobial compositions and, more specifically, relates to stable antimicrobial compositions comprising the reaction product of the reaction of polyvinylpyrrolidone (PVP) with hypochlorites.

2. Description of the Background Art

Various halogens and halogen-containing compounds have long been known for their effectiveness as bleaching agents, antiseptics, bactericides, disinfectants and the like. Such compounds such as chlorine, iodine and hypochlorites, have been used previously to destroy pathogens including various bacteria and other microorganisms. However, halogens and halogen-containing compounds are known to have several disadvantages. For example, since they are typically strong oxidizing and/or halogenating agents, they tend to be very reactive with certain materials, such as plastics, dyes and tints, metallic surfaces, and certain organic matter. Because many of these compounds are volatile, have volatile components, or have a highly reactive nature, they are typically difficult if not impossible to dry into a solid. With a few exceptions, halogens and halogen-containing compounds are generally toxic and/or strong irritants to animal tissue and exhibit an offensive odor. Thus, for all of the reasons cited above, halogens and halogen-containing compounds have met with limited commercial success as disinfectants.

It is also known that iodine and bromine can be complexed with PVP. PVP-iodine complexes are the best known of these compounds. These complexes may be used as disinfectants and preservatives with much of their aseptic properties resulting from the slow release of active halogen. However, these halogen-containing complexes also have known disadvantages causing them to be unsuitable for many commercial applications. Most notably, these compounds exhibit loss of halogen or halide ion over time, especially when heated and/or dried. Further, PVP-iodine complexes have a characteristically undesirable color and odor.

Accordingly, the present invention provides a highly stable, broad spectrum antimicrobial composition having an improved therapeutic index (i.e. improved safety and efficacy), particularly when compared with conventional hypochlorites. The PVP-hypochlorite reaction products of this invention unexpectedly exhibit a high degree of antimicrobial activity without the harmful or undesirable bleaching or extreme reactivity exhibited by typical halogen-containing compounds. Further, the reaction products of the present invention do not exhibit an offensive odor and can be dried to a stable solid, having high solubility in both polar and nonpolar solvents. The resulting solid can be used to prepare colorless antimicrobial solutions.

SUMMARY OF THE INVENTION

The present invention provides a composition of matter comprising the reaction product from the reaction of PVP and hypochlorite wherein substantially all of the hypochlorite is reacted with the PVP.

Also provided is a process for preparing a PVP-hypochlorite compound and antimicrobial compositions containing the PVP-hypochlorite compounds.

DETAILED DESCRIPTION OF THE INVENTION

The present invention is the reaction product of two reactants; PVP and hypochlorite. Polyvinylpyrrolidone (PVP), 1-ethenylpyrrolidin-2-one homopolymer, is a known compound and a staple article of commerce. The number average molecular weight of the polymer useful in this invention can range from about 1,000 to about 4,000,000 with about 10,000 to about 360,000 being preferred and about 25,000 to about 30,000 being most preferred. While PVP is the preferred agent of this invention, other agents are believed to be useful, with varying degrees of suitability, herein. For example, contemplated equivalents of PVP include copolymers of PVP, lactam-containing polymers, and polyoxyethylene and polyoxypropylene polymers or copolymers.

Hypochlorites, as used herein, refers to inorganic and organic hypochlorites having the general formula $X(OCl)_n$ wherein X is an alkali metal, an alkaline earth metal or an organic functional group, and n is a number which satisfies the valence requirements of X.

Generally, the inorganic hypochlorites include, for example, the alkali metal hypochlorites such as sodium, potassium, and lithium hypochlorites, and the alkaline earth hypochlorites such as magnesium and calcium hypochlorites. Typical organic hypochlorites include for example alkyl hypochlorites wherein the alkyl group contains from 1 to 6 carbon atoms. Further, the hypochlorites described above can be used in combination.

The preferred hypochlorites of the present invention are the alkali metal hypochlorites with sodium hypochlorite being most preferred.

The ratio of PVP to hypochlorite is typically from about 1:100 to about 1:0.0001, on a weight-to-weight basis, depending on the particular hypochlorite(s) and the molecular weight of the PVP selected. The ratio of the composition should be such that substantially all, preferably essentially all, of the free hypochlorite is reacted with the PVP polymer. The ratios of PVP to hypochlorite can be optimized to ensure that all of the hypochlorite is reacted with the PVP, by using the following simple technique. One skilled in the art can simply react the PVP with hypochlorite in the presence of a anthraquinone dye, such as Procion ® Blue dye MX-R available from ICI America, Inc. and Reactive Blue 4 available from Aldrich Chemical Company, each having a color index of 61205, until the hypochlorite no longer decolorizes the dye. Typically, the reaction is conducted as follows. To an aliquot of the aqueous reaction medium of the PVP-hypochlorite reactants is added enough dye to give an absorbance at 595 nm of 1.000 on a spectrophotometer. A stable absorbance for more than about 30 minutes indicates that the reaction is complete since any bleaching of the dye is the result of free hypochlorite reacting with the dye.

In a preferred embodiment of the present invention, the PVP will have a molecular weight of between about 25,000 and about 30,000 and the weight ratio of the final composition is not more than about 1 part PVP to about 0.1 part of sodium hypochlorite. When the PVP and the sodium hypochlorite are reacted in these ratios, as taught below, essentially all of the hypochlorite is bound to the PVP polymer. While not intending to be bound to theory, it is believed that the hypochlorite molecule reacts at the amido linkages of the PVP polymer to form a new compound exhibiting antimicrobial activity without releasing reactive amounts of hypochlorite.

In another embodiment of this invention, the PVP-hypochlorite compounds can be prepared as a solid, stable, white powder which can be made into tablets and can be readily dissolved in suitable solvents. These compounds can be dissolved in either polar or nonpolar solvents, preferably water, and can be used in various concentrations to achieve a disinfecting and/or preserving activity as desired. For these reasons, the present invention can be employed in a wide range of applications not suitable for conventional hypochlorites or PVP-halogen complexes.

As described above, the present compounds exhibit broad spectrum antimicrobial activity. Antimicrobial activity can be microbicidal or microbistatic activity. Generally, the compounds are used as disinfectants or preservatives. As used herein, disinfection occurs when the microorganism population is reduced after being in contact with the PVP-hypochlorite reaction product of the present invention. Preferably, disinfection is the ability to reduce the microbial burden by at least one log order in four hours and, more preferably, by one log order in thirty minutes.

A surprising advantage of the present composition is its unreactive nature and its low cytotoxicity particularly when compared to conventional hypochlorites. For example, conventional hypochlorites are known to react with certain metals, proteins, celluloses, hydrophilic polymers, dyes and the like while the PVP-hypochlorite reaction products have exhibited essentially no reactivity with the materials tested. Moreover, at comparable concentrations, the PVP-hypochlorite reaction products have been shown to exhibit much lower cytotoxicity than hypochlorites. The present reaction products have also been shown to provide an unexpectedly high degree of antimicrobial activity when compared to PVP-chlorine complexes under similar conditions.

The PVP-hypochlorite reaction products are prepared by dissolving the PVP in water and adding a standardized 5% hypochlorite solution (using standard procedures such as USP XXII, p. 1261) to the mixture. The mixture is heated to a temperature of between about 10° C. and about 100° C. for about 140 hours to about 1 hour respectively. Preferably, the mixture is heated from about 35° C. to about 70° C. for about 50 hours to about 5 hours, respectively. After heating, the mixture is cooled and the resulting solution can be tested for completion of the reaction by using the anthraquinone dye test described above. The final PVP-hypochlorite reaction solution may be used without modification. Optionally, the reaction solution can be either concentrated or diluted in a suitable solvent and aqueous solutions containing 2.5% by weight of the PVP-hypochlorite reaction product have exhibited a high degree of antimicrobial activity. The PVP-hypochlorite reaction products can also be separated from the reaction mixture by conventional means such as evaporation, filtration or dialysis, solvent extraction and the like.

In another embodiment of the invention, the final reaction solution can be evaporated to dryness under reduced pressure and/or elevated temperatures to obtain a solid PVP-hypochlorite material which may then be stored, transported, tableted and/or mixed into aqueous or organic solvents. The final solid reaction product is typically glassy and is somewhat hygroscopic. Antimicrobial compositions can be prepared containing from about 0.00001% to about 50% and preferably 10% to 0.0001% by weight of the PVP-hypochlorite reaction products depending on the application and the purpose (i.e. disinfecting or preserving) employed.

In order to test the antimicrobial activity of the present composition, the following experiments were conducted.

Example 1

A PVP-hypochlorite reaction product was prepared by dissolving 50 grams of K25 providone, USP (average molecular weight of 25,000) available from GAF Corporation in 700 ml. of distilled water. A 5% NaOCl solution was standardized using the procedure in USP XXII, page 1261. Enough standardized NaOCl was added to the aqueous mixture to obtain 5 grams (0.0676 mole.) of NaOCl. Purified water was added to the mixture to raise the volume of mixture to 1000 ml.

The final mixture was heated at 56° C. for 6 hours. After heating, the mixture was allowed to cool to room temperature. A sample of the cooled solution was tested to ensure completion of the reaction by adding to the sample an amount of Procion ® Blue MXR to give an absorbance of about 1.000 at 585 nm as measured by spectrophotometer. The reaction was completed since there was no loss of color in the sample when compared to a Procion Blue ® MX-R standard. The reaction product of PVP and hypochlorite was obtained in a 5% aqueous solution.

Aqueous solutions containing the PVP-hypochlorite reaction product of this invention were prepared in order to study their antimicrobial activity. Each solution was evaluated for the log kill rate of three test organisms; *Serratia marcescens*, *Candida albicans*, and *Aspergilius fumigatus*.

Examples 2-5

Examples 2-5 were prepared as described in Example 1 except that the reaction conditions were modified as shown in Table I.

Four aqueous solutions were prepared having the compositions identified in Table I. All percentages indicated throughout these Examples are in weight/weight ratios unless otherwise indicated. The PVP-hypochlorite solutions obtained from Examples 1-5 were diluted with an equal weight of distilled water. To each solution was added 0.05% $Na_2HPO_4$ and HCl, to adjust pH.

The antimicrobial activity of the above solutions was tested by exposing the test organism at about $1.0 \times 10^6$ to about $1.0 \times 10^7$ colony forming units per milliliter (CFU/ml.) to 10 ml. of each composition at room temperature for time intervals of 15 or 20 minutes, and 30 minutes. An aliquot of each inoculated sample was removed at the measured time, diluted in a neutralizing broth (Dey-Engley) and plated with neutralizing agar. The agar plates were incubated for 2 to 5 days and plate counts were determined to calculate reduction in CFU/ml. for each organism. The calculated log order reductions are also shown in Table I. Log order reductions of about 4.2 to 4.5 are generally considered total kill.

TABLE I

PVP-SODIUM HYPOCHLORITE SOLUTIONS AND THEIR ANTIMICROBIAL ACTIVITY

| EXAMPLE | PVP NaOCl (wt./wt. %) | REACTION CONDITION (temp/time) | $Na_2HPO_4$ (wt. %) | pH | OSMOLAL mOsm/Kg |
|---|---|---|---|---|---|
| 2 | 2.5:0.25 | 23° C./4 Day | 0.05 | 7.16 | 210 |
| 3 | 2.5:0.25 | 37° C./1 Day | 0.05 | 7.21 | 248 |
| 4 | 2.5:0.25 | 56° C./6 Hour | 0.05 | 7.21 | 248 |
| 5 | 2.5:0.25 | 70° C./6 Hour | 0.05 | 7.21 | 250 |

| | LOG REDUCTIONS | | | | | |
|---|---|---|---|---|---|---|
| | S. marcenscens | | C. albicans | | A. fumigatus | |
| EXAMPLE | 15 min | 30 min | 20 min | 30 min | 15 min | 30 min |
| 2 | 4.2 | >4.5 | >4.4 | >4.4 | 1.8 | 3.8 |
| 3 | >4.5 | >4.5 | 4.4 | >4.4 | 3.9 | >4.3 |
| 4 | >4.5 | >4.5 | >4.4 | 3.3 | 3.4 | 3.0 |
| 5 | 3.7 | >4.5 | 4.1 | >4.4 | 0.9 | 2.2 |

As shown in Table I, the 2.5%:0.25% PVP-sodium hypochlorite solutions exhibited a high degree of microbiocidal activity.

The present reaction products have a variety of uses, including but not limited to, industrial and commercial cleaning and disinfecting compositions for medical, dental, and food manufacturing equipment; cleaning and disinfecting compositions for commercial and home use; preservations for industrial products, cosmetics, soaps, shampoos, oral care products, and ophthalmic products.

It should be understood that the scope of the subject invention is not limited to the examples set forth above and includes equivalent, embodiments, modifications and variations that fall within the scope of the attached claims.

What is claimed is:

1. An antimicrobial composition of matter comprising the reaction product from the reaction of polyvinylpyrrolidone and hypochlorite wherein the ratio of polyvinylpyrrolidone to hypochlorite is from about 1:100 to about 1:0.0001 by weight and wherein substantially all of the hypochlorite is reacted with the polyvinylpyrrolidone.

2. The composition of claim 1 wherein the polyvinylpyrrolidone has a number average molecular weight of between about 10,000 and about 360,000.

3. The composition of claim 2 wherein the hypochlorite is an alkali metal hypochlorite, an alkaline earth hypochlorite, or combination thereof.

4. The composition of claim 3 wherein the hypochlorite is an alkali metal.

5. The composition of claim 4 wherein the hypochlorite is sodium hypochlorite.

6. The composition of claim 1 wherein said composition is a solid.

7. An aqueous composition containing a disinfecting amount of the reaction product from the reaction of polyvinylpyrrolidone and hypochlorite.

8. A method for preparing a polyvinylpyrrolidone-hypochlorite compound comprising reacting polyvinylpyrrolidone and hypochlorite in a ratio of about 1:100 to about 1:0.0001 by weight in a suitable solvent and reacting said polyvinyl-pyrrolidone and said hypochlorite at temperatures between about 10° C. and about 100° C. for about 1 hour to about 130 hours.

9. The method of claim 8 wherein said solvent is water.

10. The method of claim 8 further comprising separating the resulting polyvinylpyrrolidone-hypochlorite reaction product from said solution.

11. The method of claim 10 wherein said separation step occurs by evaporation.

12. A composition prepared by the method of claim 9.

13. An antimicrobial composition comprising water and from about 0.0001% to about 10% by weight of the reaction product from the reaction of polyvinylpyrrolidone with hypochlorite, said reaction product prepared by contacting said polyvinylpyrrolidone with said hypochlorite in ratios of about 1:100 to about 1:0.0001 by weight under temperatures from about 10° C. to about 100° C. for about 1 hour to about 130 hours.

14. A method for disinfecting ar organic material comprising contacting said material with composition containing an effective amount of the reaction product of polyvinylpyrrolidone and hypochlorite for a time sufficient to disinfect said material.

15. A method for controlling the microbial growth in a composition comprising mixing into said composition an effective amount of the reaction product of polyvinylpyrrolidone with hypochlorite to provide antimicrobial activity.

16. An antimicrobial composition of matter comprising the reaction product from the reaction of polyvinylpyrrolidone and hypochlorite, wherein the polyvinylpyrrolidone has a number average molecular weight of between about 1,000 to about 4,000,000 and the hypochlorite is selected from the group consisting of an alkali metal hypochlorite, an alkaline earth hypochlorite or a combination thereof, and wherein the ratio of polyvinylpyrrolidone to hypochlorite on a weight basis is from about 1:100 to about 1:0.0001.

* * * * *